United States Patent [19]
Ritacco

[11] Patent Number: 4,582,608
[45] Date of Patent: Apr. 15, 1986

[54] HPLC COLUMN

[75] Inventor: Robert P. Ritacco, Saunderstown, R.I.

[73] Assignee: Separations Technology, Inc., R.I.

[21] Appl. No.: 702,057

[22] Filed: Feb. 15, 1985

[51] Int. Cl.⁴ .............................................. B01D 15/08
[52] U.S. Cl. ...................................... 210/656; 55/386; 210/198.2
[58] Field of Search ...................... 210/656, 659, 198.2; 55/386

[56] References Cited

U.S. PATENT DOCUMENTS

| | | | |
|---|---|---|---|
| 3,230,167 | 1/1966 | Golar | 210/656 |
| 3,407,574 | 10/1968 | Perkins et al. | 55/386 |
| 3,657,864 | 4/1972 | Davis et al. | 55/386 |
| 4,354,932 | 10/1982 | McNeil | 55/386 |
| 4,450,082 | 5/1984 | Tanouchi | 210/656 |

Primary Examiner—John Adee
Attorney, Agent, or Firm—Donald Brown

[57] ABSTRACT

An HPLC column provided with structure at its inlet and outlet ends to insure optimal distribution of fluids through the media therein.

18 Claims, 9 Drawing Figures

SEPERATION MEDIA

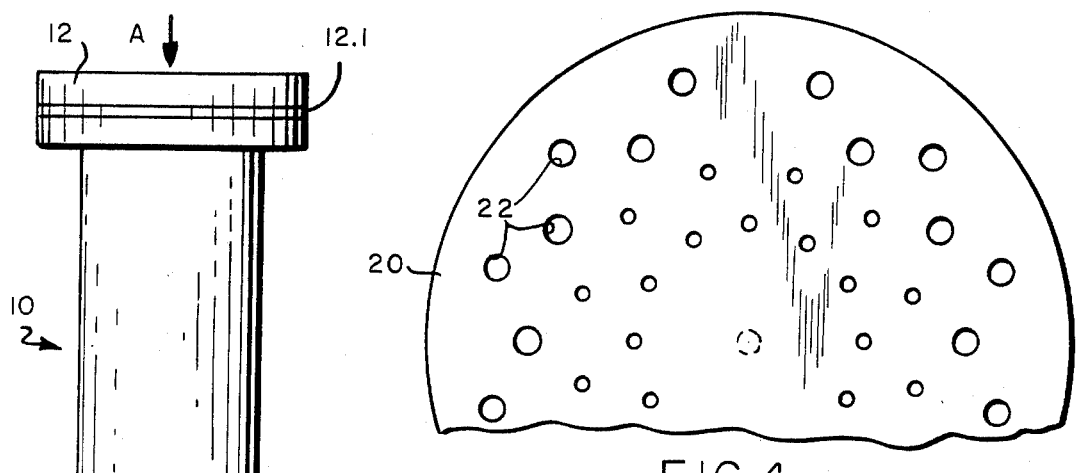
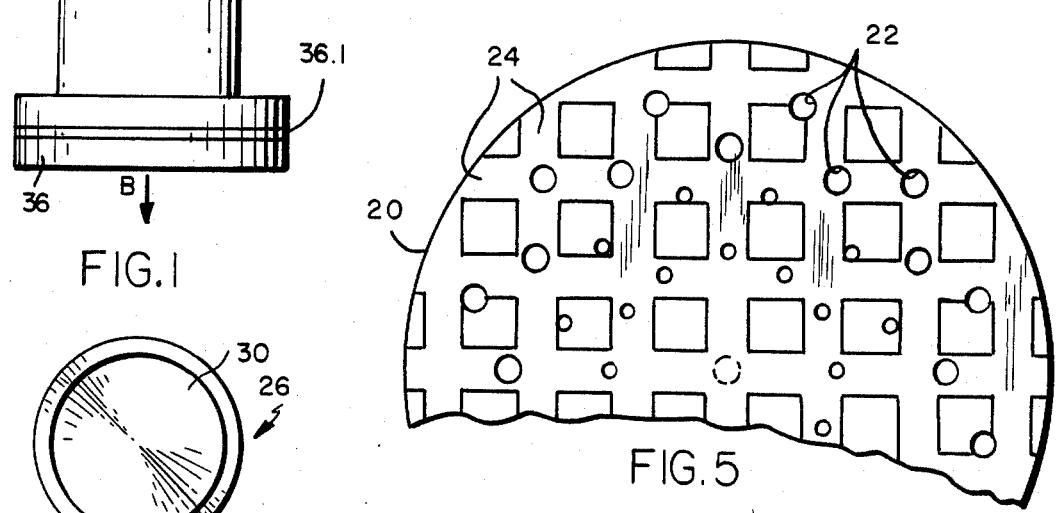
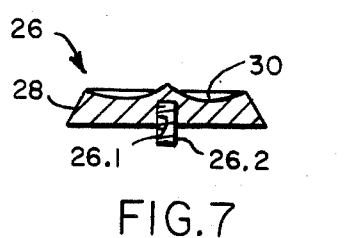
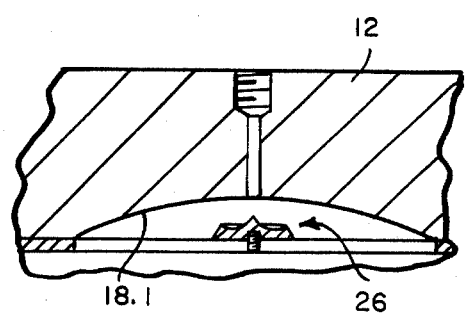
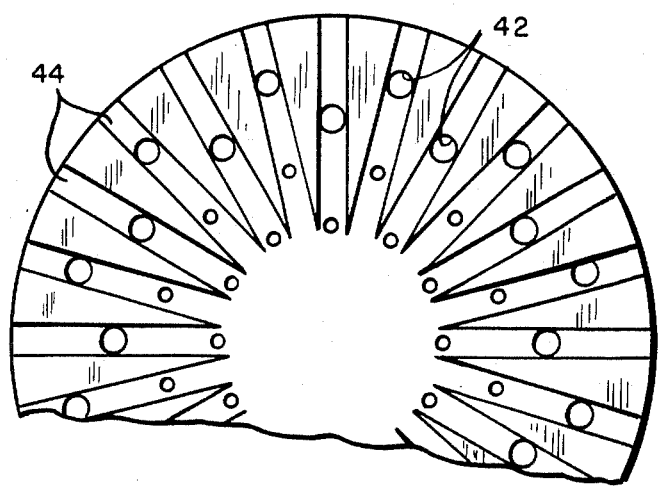

SEPERATION MEDIA

HPLC COLUMN

BACKGROUND OF THE INVENTION

HPLC columns for analyzing solutions contain separation media and it is important that the fluids undergoing analysis be delivered to the media uniformly throughout the cross-sectional area of the media to insure maximum efficiency and accuracy. Since the fluid is delivered into the column and exits through relatively small openings in the column and the latter is of relatively large cross-sectional area compared to the openings, there is a tendency for the fluid entering at the top to penetrate the media to a considerable depth before it spreads out and as it exits at the lower end to constrict, thus reducing the efficiency and effectiveness of the media. It is the purpose of this invention to so structure the column at the entrance and exit ends as to disperse the entering fluid throughout the cross-sectional area at the point of entry and maintain uniform flow through the media from top to bottom to thus take full advantage of the media.

SUMMARY OF THE INVENTION

As herein illustrated, the HPLC column according to this invention comprises a media chamber of uniform cross section having open ends and closure caps applied thereto, said media chamber containing separation media, said closure cap at the open upper end containing an inlet opening at the center thereof through which fluid is introduced into the media chamber and having at the side facing the open end of the media chamber a reentrant recess defining a dispersion chamber, a distributor plate coextensive in area with the cross-sectional area of the open end of the media chamber positioned between said open upper end and said closure, said distributor plate containing a plurality of concentric, circularly-arranged, peripherally-spaced openings of increasing size radially of the center and a dispersion member positioned in the dispersion chamber at the center of the distributor plate at the side facing the inlet opening defining a deflector surface facing the reentrant recess. The deflector surface is of toroidal configuration and the openings in adjacent circles are offset half the distance between successive openings. A wire mesh is disposed at the side of the distributor plate facing the open end of the media chamber and a sintered, porous, stainless steel disk is interposed between the wire mesh and the open end of the media chamber. The distributor plate has at the side facing the open end of the media chamber, right-angularly disposed, parallel grooves. The closure cap at the open lower end contains at the center thereof a discharge opening through which fluid is discharged and a support plate substantially coextensive in area with the cross-sectional area of the open lower end of the media chamber and containing circularly-arranged openings of increasing size radially of the center facing the open lower end and a plurality of diametrical, angularly-disposed grooves on the side facing the closure cap is disposed between the closure cap and the open lower end of the chamber. A sintered stainless steel disk is interposed between the open lower end of the media chamber and the support plate.

The invention will now be described in greater detail with reference to the accompanying drawings, wherein:

FIG. 1 is an elevation of a conventional column;

FIG. 4 is a plan view of the top side of the distributor plate at the top of the column comprising an element of the assembly;

FIG. 5 is a plan view of the bottom side of the distributor plate;

FIG. 6 is a plan view of a disperser comprising another part of the assembly;

FIG. 7 is a diametral section of FIG. 6;

FIG. 8 is a plan view of the bottom side of the support plate at the bottom of the column; and FIG. 9 is a fragmentary section at the upper end of the column showing a modification wherein the closure is provided with an arcuate recess.

Figure 2:
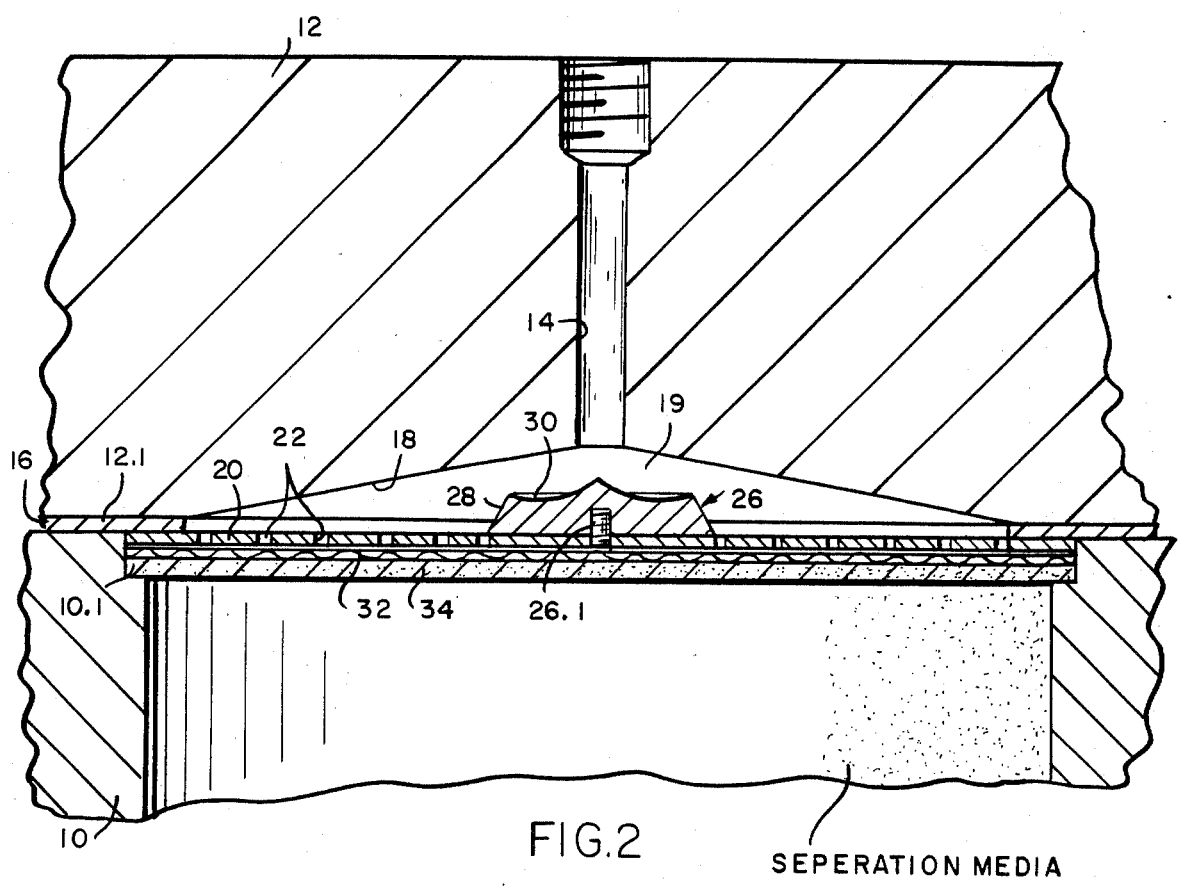
FIG. 2 is an enlarged diametral section at the inlet end of the column.

Referring to the drawings, FIG. 1, there is shown in elevation a typical HPLC column 10 of cylindrical cross section within which is packed separation media. The fluid to be analyzed is introduced into the column through the top, as indicated diagrammatically by the arrow A at the top and exits at the bottom as indicated by the arrow B at the bottom.

In accordance with this invention, the top and bottom are structured to expose the fluid or fluids to the separation media in such a way as to take maximum advantage of the separation media and to obtain optimum results. To achieve this, as herein illustrated, the column 10, FIG. 2, is provided at its upper open end wth a closure 12 containing a centrally-located opening 14 centered with respect to the cross section of the column and at the side 16 facing the open end of the column, a conical recess 18 defining a distributor chamber 19, the larger diameter of which corresponds substantially in cross section to that of the column. At the open upper end of the media chamber, there is a circular recess 10.1 within which is disposed a distributor plate 20, a wire mesh disk 32 and a sintered, porous, stainless steel disk 34. A gasket 12.1 is disposed about the recess 10.1 between the top of the column and the closure cap.

Figure 3:
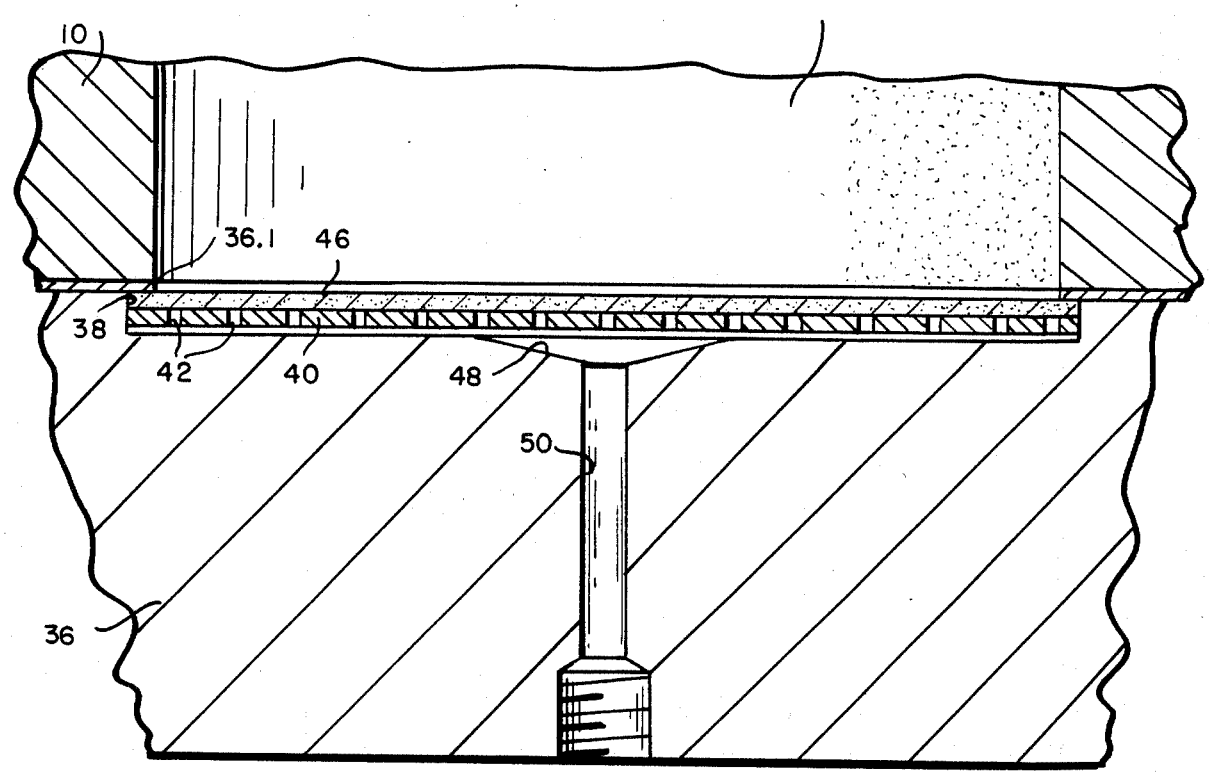
FIG. 3 is an enlarged diametral section of the outlet end of the column.

The distributor plate 20 is disposed between the closure cap 12 and the open end of the column and, as shown in FIG. 3, has in the side facing the closure cap a plurality of openings 22 distributed in uniformly-spaced relation to each other in concentric circles about the center of the distributor plate with the openings in alternate circles of openings displaced one-half the distance between openings. As shown in FIG. 3, the two centermost circles of openings are ⅛ inch and are spaced apart 30 degrees. The openings in the two outermost circles of openings are 3/16 inch and spaced apart 30 degrees. The underside of the distributor plate 20, as shown in FIG. 5, has right-angularly spaced, parallel grooves 24, 1/32 inch deep, ¼ inch wide and spaced apart ⅜ inches.

The wire mesh disk 32 is disposed in the recess 10.1 at the side of the distributor plate facing the open end of the column and the porous sintered stainless steel disk 34 is disposed between the wire mesh and the open end of the column. The stainless steel disk 34 has a porosity of 10 microns. The wire mesh disk defines a spacer between the distributor plate 20 and the stainless steel disk 34 and is of 60 mesh per inch.

A disperser part 26, FIGS. 6 and 7, is mounted in the distribution chamber 19 on the distributor plate 20 at the center thereof facing the closure of frustoconical diametral section. The disperser part 26 defines a conical peripheral surface 28 and has a toroidal upper end surface 30 facing the inlet opening 14 and concentric therewith. The lower side of the disperser part 26 is flat and contains a hole 26.1 at its center to receive an attaching pin 26.2 by means of which it is attached to the center of the distributor plate.

Functionally, the toroidally-faced disperser part 26 within the distribution chamber at the center of the distributor plate diverts the incoming stream of fluid entering through the inlet 14 against the face of the conical recess 18 so as to distribute it laterally throughout the entire area of the distributor plate and this, in conjunction with the staggered arrangement of the openings 22 in the distributor plate, the wire mesh screen 32 below the distributor plate and the porous sintered stainless steel disk 34, provides for spreading the incoming fluid over the entire area of the column and for uniform flow through the minute channels provided by the sintered stainless steel disk 34 into the media.

The separated fluids exit from the column through a bottom closure 36, FIG. 3, which contains a circular recess 38 coextensive in area with the lower open end of the column within which there is positioned a support plate 40 having at its upper side, that is, the side facing the open lower end of the column, a plurality of openings 42 arranged as are the openings 22 in the distributor plate 20. The lower side of the support plate 40, FIG. 8, is provided with a plurality of diametrically-arranged grooves 44 disposed at an angular spacing of 15 degrees to each other which are 3/16 inch in width and 1/32 of an inch deep. A sintered stainless steel disk 46 like the disk 34 at the top of the column is interposed between the open lower end of the column and the support plate 40.

The bottom of the recess 38 has at its center a frusto-conical recess 48, at the center of which there is an outlet 50 extending through the closure 36.

A gasket 36.1 is disposed about the recess 38 between the bottom of the column and the closure 36.

The structure at the lower end of the column insures uniform discharge and maximum availability of the filter media by inhibiting funneling at the lower end of the column which tends to be induced by the discharge through the outlet opening 50.

An alternative structure at the upper end of the column is shown in FIG. 9 wherein the closure 12 is provided with a recess 18.1 of arcuate section.

As thus described, the unique structure at the upper and lower ends of the column insures maximum availability of the separation media to the fluids undergoing separation and maximum efficiency in separation.

It should be understood that the present disclosure is for the purpose of illustration only and includes all modifications or improvements which fall within the scope of the appended claims.

As thus described, the unique structure at the upper and lower ends of the column insures even distribution of flow at the upper end and an even discharge of flow at the lower end particularly important at flow rates at or above 500 ml/min. in pilot plant and production systems. HPLC as used herein refers to a high performance liquid chromatography system.

What is claimed is:

1. An HPLC column comprising a media chamber of uniform cross section having open ends and closure caps applied thereto, said media chamber containing separation media, a closure cap at the open upper end containing an inlet opening at the center thereof through which fluid is introduced into the media chamber and having at the side facing the open end of the media chamber, a reentrant recess defining a dispersion chamber, a distributor plate coextensive in area with the cross-sectional area of the open end of the media chamber positioned between said open upper end and said closure, said distributor plate containing a plurality of concentric, circularly-arranged, peripherally-spaced openings of increasing size radially of the center and a dispersion member positioned in the dispersion chamber at the center of the distributor plate at the side facing the inlet opening defining a deflector surface facing the reentrant recess.

2. An HPLC column according to claim 1 wherein said deflector surface is of toroidal configuration.

3. An HPLC column according to claim 1 wherein the openings in adjacent circles are offset half the distance between successive openings.

4. An HPLC column according to claim 1 wherein a wire mesh is disposed at the side of the distributor plate facing the open end of the media chamber.

5. An HPLC column according to claim 4 wherein a sintered stainless steel disk is interposed between the wire mesh and the open end of the media chamber of 10 microns porosity.

6. An HPLC column according to claim 5 wherein the distributor plate has on the side facing the open end of the media chamber right-angularly disposed, spaced, parallel grooves.

7. An HPLC column according to claim 6 wherein the grooves are spaced apart approximately ⅜ inches, are 1/32 inches deep and ¼ inch wide.

8. An HPLC column comprising a media chamber of uniform cross section having open ends and closure caps applied thereto, said media chamber containing separation media, the closure cap at the open upper end containing at the center thereof an inlet opening through which fluid is introduced into the media chamber and having at the side facing the open end of the media chamber a conical recess defining a dispersion chamber, said open upper end of the chamber containing a circular recess coextensive with the distributor chamber, a distributor plate coextensive in area with the cross-sectional area of the open end of the media chamber positioned in said recess between said open upper end and said closure cap, said distributor plate containing a plurality of concentric, circularly-arranged, peripherally-spaced openings of increasing size radially of the center and a dispersion member positioned in the dispersion chamber at the center of the distributor plate at the side facing the inlet opening defining a deflector surface facing the conical recess and a sintered stainless steel disk interposed between the distributor plate and the bottom of the recess.

9. An HPLC column according to claim 8 wherein a wire mesh is interposed between the distributor plate and the sintered stainless steel disk.

10. An HPLC column according to claim 1 wherein the closure cap at the open lower end contains at the center thereof a discharge opening through which fluid is discharged and a support plate substantially coextensive in area with the cross-sectional area of the open lower end of the media chamber containing circularly-arranged openings of increasing size radially of the center facing the open lower end and a plurality of diametrical, angularly-disposed grooves in the side facing the closure cap.

11. An HPLC column according to claim 10 wherein a sintered stainless steel disk is interposed between the open lower end of the media chamber and the support plate.

12. An HPLC column according to claim 10 wherein said angularly-disposed grooves are 3/16 inches wide, 1/36 inch deep and spaced angularly 15 degrees apart.

13. An HPLC column according to claim 1 wherein the reentrant recess is of conical configuration.

14. An HPLC column according to claim 1 wherein the reentrant recess is of arcuate configuration.

15. The method of dispersing fluid entering a vessel through an opening thereof of smaller cross-sectional area than that of the vessel to cause the fluid to be dispersed substantially uniformly throughout the cross-sectional area of the vessel comprising providing a concave recess in concentric relation to the inlet opening defining a distribution chamber at the end of the vessel, positioning a deflector within the recess opposite the entrance having a surface spaced from the inlet and concentric therewith and injecting the fluid to be dispersed in the vessel through said opening therein into engagement with the face of the distributor at a pressure such as to cause the fluid to be reversely deflected into engagement with the concave surface of the recess.

16. The method according to claim 15 comprising providing a distributor with a concave surface recess of conical configuration.

17. The method according to claim 15 comprising providing a distributor with a concave surface recess of arcuate configuration.

18. The method according to claim 15 comprising providing a distributor with a surface of toroidal configuration.

* * * * *